United States Patent
Chen et al.

(10) Patent No.: US 12,369,957 B2
(45) Date of Patent: Jul. 29, 2025

(54) REPAIR DEVICE FOR PROXIMAL HUMERAL FRACTURE

(71) Applicant: CHINESE PLA GENERAL HOSPITAL, Beijing (CN)

(72) Inventors: Hua Chen, Beijing (CN); Peifu Tang, Beijing (CN)

(73) Assignee: CHINESE PLA GENERAL HOSPITAL, Beijing (CN)

(*) Notice: Subject to any disclaimer, the term of this patent is extended or adjusted under 35 U.S.C. 154(b) by 0 days.

(21) Appl. No.: 18/833,945

(22) PCT Filed: Aug. 5, 2022

(86) PCT No.: PCT/CN2022/110473
§ 371 (c)(1),
(2) Date: Jul. 29, 2024

(87) PCT Pub. No.: WO2023/142423
PCT Pub. Date: Aug. 3, 2023

(65) Prior Publication Data
US 2025/0107831 A1    Apr. 3, 2025

(30) Foreign Application Priority Data
Jan. 29, 2022   (CN) .......................... 202210111661.6

(51) Int. Cl.
*A61B 17/72* (2006.01)
(52) U.S. Cl.
CPC .............................. *A61B 17/7233* (2013.01)

(58) Field of Classification Search
None
See application file for complete search history.

(56) References Cited

U.S. PATENT DOCUMENTS 5,041,114 A * 8/1991 Chapman ............. A61B 17/744
606/291
5,356,410 A * 10/1994 Pennig ................. A61B 17/746
606/62

(Continued)

FOREIGN PATENT DOCUMENTS

CN        202086563 U     12/2011
CN        104083198 A     10/2014
(Continued)

*Primary Examiner* — Ann Hu
(74) *Attorney, Agent, or Firm* — Bayramoglu Law Offices LLC

(57) ABSTRACT

A repair device for a proximal humeral fracture includes a stable structure, and the stable structure is connected to a humerus through a humeral medullary cavity supporting portion, a first insertion body, a fitting portion, and a second insertion body. The first insertion body is coupled to the second insertion body, the first insertion body is connected to a humeral head, and the second insertion body is clamped on the fitting portion. After the repair device is implanted into a body of a patient, a fractured site of the patient almost can take full-range early activities upon a surgery. A threaded end of the first insertion body is fixedly connected to the humeral head to realize fixed connection between the repair device and the humeral head. The second insertion body is connected to the first insertion body in an adjustable manner.

16 Claims, 6 Drawing Sheets

(56) References Cited

U.S. PATENT DOCUMENTS

| | | | | |
|---|---|---|---|---|
| 5,443,466 A * | 8/1995 | Shah | | A61B 17/72 |
| | | | | 606/62 |
| 5,702,486 A | 12/1997 | Craig et al. | | |
| 5,776,194 A * | 7/1998 | Mikol | | A61F 2/4014 |
| | | | | 606/62 |
| 7,294,130 B2 * | 11/2007 | Orbay | | A61B 17/8057 |
| | | | | 606/291 |
| 7,927,333 B2 * | 4/2011 | Gradl | | A61B 17/746 |
| | | | | 606/86 R |
| 7,938,850 B2 * | 5/2011 | Orbay | | A61B 17/8061 |
| | | | | 606/291 |
| 8,568,462 B2 * | 10/2013 | Sixto, Jr. | | A61B 17/8061 |
| | | | | 606/86 R |
| 8,709,092 B2 * | 4/2014 | Segina | | A61F 2/3609 |
| | | | | 606/70 |
| 9,463,054 B2 * | 10/2016 | Mueckter | | A61B 17/7241 |
| 9,610,073 B2 * | 4/2017 | Bonutti | | A61B 17/7059 |
| 9,795,412 B2 * | 10/2017 | Sinha | | A61B 17/863 |
| 9,883,948 B2 * | 2/2018 | Chavarria | | A61F 2/4014 |
| 9,907,586 B2 * | 3/2018 | Levy | | A61B 17/72 |
| 11,751,922 B2 * | 9/2023 | Roche | | A61B 17/7283 |
| | | | | 606/64 |
| 11,944,361 B2 * | 4/2024 | Hamel | | A61B 17/8004 |
| 12,042,200 B2 * | 7/2024 | Rossney | | A61B 17/744 |
| 2006/0173458 A1 * | 8/2006 | Forstein | | A61B 17/1728 |
| | | | | 606/281 |
| 2017/0042592 A1 * | 2/2017 | Kim | | A61B 17/744 |
| 2017/0056081 A1 * | 3/2017 | Langdale | | A61B 17/72 |
| 2018/0028241 A1 | 2/2018 | Levy | | |

FOREIGN PATENT DOCUMENTS

| | | | | | |
|---|---|---|---|---|---|
| CN | 213310612 U | | 6/2021 | | |
| CN | 114533234 A | | 5/2022 | | |
| JP | 2006247400 A | * | 9/2006 | | A61B 17/746 |
| JP | 2007518537 A | * | 7/2007 | | |
| WO | WO-2006081483 A1 | * | 8/2006 | | A61B 17/1717 |
| WO | WO-2010031098 A2 | * | 3/2010 | | A61B 17/72 |
| WO | WO-2012003884 A1 | * | 1/2012 | | A61B 17/56 |
| WO | WO-2013075730 A1 | * | 5/2013 | | A61B 17/72 |
| WO | WO-2014134669 A1 | * | 9/2014 | | A61B 17/8033 |
| WO | WO-2023009094 A1 | * | 2/2023 | | |

* cited by examiner

REPAIR DEVICE FOR PROXIMAL HUMERAL FRACTURE

CROSS REFERENCE TO THE RELATED APPLICATIONS

This application is the national phase entry of International Application No. PCT/CN2022/110473, filed on Aug. 5, 2022, which is based upon and claims priority to Chinese Patent Application No. 202210111661.6, filed on Jan. 29, 2022, the entire contents of which are incorporated herein by reference.

TECHNICAL FIELD

The present disclosure relates to the technical field of medical devices for orthopedic surgeries, and in particular to a repair device for a proximal humeral fracture.

BACKGROUND

The proximal humeral fracture is a clinical common fracture. With an ever-increasing incidence rate, it has become difficult to treat in traumatic orthopedics. For the proximal humeral fracture, one of the common surgical solutions is to place an intramedullary nail in the humerus. However, the intramedullary nail is limited when fixing the humeral head. For the severe comminuted fracture, there lacks stable fixation to provide an effective mechanical support for early functional exercises of the shoulder joint. In addition, the implantation of the intramedullary nail involves drilling to form an entry point. Moreover, the intramedullary nail does not match with an internal structure of the medullary cavity obviously, which has an impact on intramedullary blood supply. In view of this, in order to better support the humeral head, a fixation device with a larger supporting area is provided by the inventor of the present disclosure to replace the intramedullary nail (refer to the Chinese Patent Application No. 201410342347.4). The fixation device achieves a desirable supporting effect over the intramedullary nail. The device provides a supporting surface at a specific angle, and is fixedly connected to the humeral head through a main nail connected to the humeral head. It is found that, in use, the fixing effect of the fixation device is undesirable for the undesirable overall strength. After the fixation device is implanted into the body of the patient, the fractured site of the patient must rest for a period of time before taking part in activities, which is unfavorable for recovery of related joints of the fractured site. In addition, after the fixation device is connected to the humeral head through the main nail, it is difficult to finely adjust the position of the humeral head.

Therefore, how to provide a repair device to overcome the above-defects is a technical problem to be solved urgently by those skilled in the art.

SUMMARY

A technical problem to be solved by the present disclosure is to provide a repair device with a higher strength and a better fixation supporting effect, such that the repair device is stably coupled to a fractured site. The technical solutions are as follows:

A repair device for a proximal humeral fracture includes:
a humeral medullary cavity supporting portion, where the humeral medullary cavity supporting portion is provided with a proximal end, the proximal end is adjacent to a shoulder, the proximal end includes a humeral head supporting surface configured to support a humeral head internally, and a first through hole penetrating through the humeral head supporting surface is formed at the proximal end;
a first insertion body, where two ends of the first insertion body are respectively provided with a threaded end and a male coupling end, the male coupling end is provided with an internal thread or an external thread, and the first insertion body can be inserted into the first through hole, with the threaded end allowed to be screwed into the humeral head;
a fitting portion, where the fitting portion includes a fitting surface allowed to be fitted to an outer sidewall of a humerus and an outer side surface opposite to the fitting surface, a position fitted to the outer sidewall of the humerus is a position on the outer sidewall of the humerus away from the humeral head and adjacent to a greater tubercle and a lesser tubercle, a second through hole penetrating through the fitting surface is formed in the fitting portion, and when the fitting portion is fitted to the outer sidewall of the humerus, the second through hole is coaxial with the first through hole; and
a second insertion body, where two ends of the second insertion portion are respectively provided with a female coupling end and a clamping end, the female coupling end is provided with an external thread or an internal thread matching with the internal thread or the external thread of the male coupling end, and when the second insertion body is inserted into the second through hole, the clamping end is clamped in the second through hole and located at the outer side surface of the fitting portion, and the female coupling end is coupled to the male coupling end, such that a coupled position for the male coupling end and the female coupling end can be adjusted through the clamping end, thereby adjusting a position of the humeral head.

Preferably, the fitting portion is a sheet structure; the sheet structure includes a top side, a bottom side, as well as a left side and a right side that are located between the top side and the bottom side and configured to connect the top side and the bottom side; when the sheet structure is fitted to the outer sidewall of the humerus, the top side is adjacent to the proximal end, the bottom side is away from the proximal end, the left side is adjacent to the greater tubercle, and the right side is adjacent to the lesser tubercle; a direction from the top side to the bottom side is a length direction; a length from the top side to the bottom side along the length direction is 3-6 cm; a direction from the left side to the right side is a width direction; and a width from the left side to the right side along the width direction is 2-4 cm.

Preferably, a plurality of rotator cuff suture line through holes penetrating through the fitting surface and the outer side surface are formed at a position of the sheet structure adjacent to the top side, and configured to allow a rotator cuff suture line to pass through to suture a rotator cuff on the sheet structure; a third through hole penetrating through the fitting surface and the outer side surface is formed at a position of the sheet structure adjacent to the bottom side; the repair device further includes a rotator cuff counteracting bolt; the rotator cuff counteracting bolt can pass through the third through hole, with a threaded tail allowed to be fixedly connected to the humerus; and an end of the rotator cuff counteracting bolt is clamped in the third through hole and located at the outer side surface of the sheet structure.

Preferably, the humeral head is provided with a lower edge away from the proximal end; the lower edge is connected to a humeral shaft located under the lower edge; and an axial direction of the third through hole is toward the humeral shaft within a range of 1-3.5 cm to the lower edge, such that the tail of the rotator cuff counteracting bolt can be fixedly connected to the humeral shaft within the range of 1-3.5 cm to the lower edge.

Preferably, the third through hole is a through hole with leftward incline and downward arrangement; the leftward incline is formed by deviating an axial direction of the through hole to the left side by an angle of 10-30° from a vertical axial direction perpendicular to the fitting surface of the sheet structure; and the downward arrangement is formed by deviating the axial direction of the through hole to the bottom side by an angle of 5-40° from the vertical axial direction perpendicular to the fitting surface of the sheet structure.

Preferably, the position of the sheet structure adjacent to the top side includes an edge of the sheet structure adjacent to the top side and along the width direction, an edge of the sheet structure adjacent to the top side, adjacent to the left side and along the length direction, and an edge of the sheet structure adjacent to the top side, adjacent to the right side and along the length direction.

Preferably, two greater tubercle through holes penetrating through the fitting surface and the outer side surface are formed at a position of the sheet structure adjacent to the left side along the length direction; two lesser tubercle through holes penetrating through the fitting surface and the outer side surface are formed at a position of the sheet structure adjacent to the right side along the length direction; the repair device further includes two greater tubercle fixing bolts and two lesser tubercle fixing bolts; the greater tubercle fixing bolt can pass through the greater tubercle through hole, with a threaded tail allowed to be fixedly connected to the greater tubercle; an end of the greater tubercle fixing bolt is clamped in the greater tubercle through hole and located at an outer side surface of the sheet structure; the lesser tubercle fixing bolt can pass through the lesser tubercle through hole, with a threaded tail allowed to be fixedly connected to the lesser tubercle; an end of the lesser tubercle fixing bolt is clamped in the lesser tubercle through hole and located at the outer side surface of the sheet structure.

Preferably, the greater tubercle through hole is a through hole with leftward incline; the leftward incline is formed by deviating an axial direction of the through hole to the left side by an angle of 10-30° from a vertical axial direction perpendicular to the fitting surface of the sheet structure; the lesser tubercle through hole is a through hole with rightward incline; and the rightward incline is formed by deviating an axial direction of the through hole to the right side by an angle of 10-30° from the vertical axial direction perpendicular to the fitting surface of the sheet structure.

Preferably, the second through hole is formed at a position of the sheet structure adjacent to a middle along the length direction, and located among the third through hole, the greater tubercle through hole and the lesser tubercle through hole.

Preferably, the humeral medullary cavity supporting portion further includes a vertical portion connected to the proximal end and extending away from the proximal end; when the sheet structure is coupled and each bolt is provided on the humeral medullary cavity supporting portion, the proximal end is provided in the width direction with a width allowed to avoid the greater tubercle fixing bolt and the lesser tubercle fixing bolt, and the vertical portion is provided in the width direction with a width allowed to avoid the rotator cuff counteracting bolt; at least one horizontal through hole extending along a horizontal direction is formed in the vertical portion; the repair device further includes at least one insertion bolt matching with the horizontal through hole in number; and the insertion bolt can be in one-to-one correspondence with the horizontal through hole, with a threaded end allowed to be screwed into the humeral shaft.

Preferably, the first insertion body is hollow, such that a guiding needle can pass through the first insertion body and the first insertion body is inserted into the first through hole through the guiding needle; the internal thread is provided in a hollow rod of the male coupling end of the first insertion body; the female coupling end of the second insertion body is a rod provided with the external thread; and the external thread can be threadedly connected to the internal thread.

Preferably, an axial direction of the first through hole is perpendicular to the humeral head supporting surface.

Preferably, the humeral head supporting surface is a supporting plane, and is formed at an angle of 45-50° with a medullary cavity.

Preferably, the proximal end includes a humeral head supporting member and a greater tubercle supporting member; the humeral head supporting surface is provided on the humeral head supporting member; the greater tubercle supporting member and the humeral head supporting member are split; the greater tubercle supporting member is provided with a protrusion toward the greater tubercle and allowed to support the greater tubercle; a position of the humeral head supporting member toward the greater tubercle supporting member is provided with a first coupling portion; a position of the greater tubercle supporting member toward the humeral head supporting member is provided with a second coupling portion; and the first coupling portion is coupled to the second coupling portion, such that the greater tubercle supporting member can be connected to the humeral head supporting member.

Preferably, the repair device further includes:
a locating portion, where two ends of the locating portion are respectively provided with a first locating end and a second locating end; a position of the proximal end away from the humeral head supporting surface is provided with a third coupling portion; and when the first coupling portion is not coupled to the second coupling portion, the first locating end of the locating portion can be detachably connected to the third coupling portion; and
a guiding portion, where the guiding portion includes an upper end and a lower end; a position of the guiding portion adjacent to the upper end is provided with an upper coupling portion; the second locating end can be detachably connected to the upper coupling portion; a first guiding through hole is formed in the guiding portion, and configured to guide the first insertion body to be inserted into the first through hole; at least one second guiding through hole is further formed in the guiding portion; and the second guiding through hole is configured to guide the insertion bolt to be inserted into the horizontal through hole.

When the first locating end of the locating portion is coupled to the third coupling portion of the proximal end and the second locating end of the locating portion is coupled to the upper coupling portion of the guiding portion, a stable structure is formed by sequentially connecting the humeral medullary cavity supporting portion, the locating portion and the guiding portion; and a direction from the upper end of the guiding portion to the lower end of the guiding portion is a vertical direction parallel to the vertical portion, an axial direction of the first guiding through hole coincides with the axial direction of the first through hole, and an axial direction of the second guiding through hole coincides with an axial direction of the corresponding horizontal through hole.

Preferably, each of two sides of the position of the humeral head supporting member toward the greater tubercle supporting member is provided with a convex step to form the first coupling portion; a corresponding position of the greater tubercle supporting member toward the convex step is provided with a matching concave step to form the second coupling portion; the second coupling portion is lapped on the first coupling portion, such that the humeral head supporting member can fixedly support the greater tubercle supporting member; a recess is formed between two convex steps of forming the first coupling portion; two coupling insertion blind holes arranged side by side are formed in the recess; a threaded blind hole is formed between the two coupling insertion blind holes; and the coupling insertion blind holes form the third coupling portion;

two guiding insertion blind holes are formed at a position of the guiding portion adjacent to the upper end; the guiding insertion blind holes form the upper coupling portion; and a through hole is formed between the two guiding insertion blind holes; and the locating portion includes a hollow rod and a locating rod; each of two ends of the hollow rod is provided with two insertion protrusions to form the first locating end and the second locating end; the two insertion protrusions of the first locating end are inserted into the two insertion blind holes of the third coupling portion; the two insertion protrusions of the second locating end are inserted into the two guiding insertion blind holes of the guiding portion; one end of the locating rod is a threaded end; the threaded end passes through the hollow rod and is threadedly connected to the threaded blind hole; and the other end of the locating rod is a clamping end, and is clamped at an outer side of an end of the locating rod adjacent to the guiding portion.

The present disclosure achieves the following technical effects:

When the repair device is used by a fractured patient, a structure connected to the humeral head, formed by the humeral medullary cavity supporting portion, the first insertion body, the second insertion body and the fitting portion, and having a high overall stability is formed. While connected to the humeral head, the first insertion body is fixedly connected to the second insertion body clamped on the fitting portion, with a high strength. After the repair device is implanted into the body of the patient, the fractured site of the patient almost can take full-range early activities upon a surgery, which is favorable for recovery of the joint at the fracture repaired site. The threaded end of the first insertion body is fixedly connected to the humeral head to realize fixed connection between the repair device and the humeral head. The second insertion body is connected to the first insertion body in an adjustable manner. Through the second insertion body, the position of the humeral head fixedly connected to the first insertion body can be adjusted. This can realize accurate location on the humeral head at the fracture in the surgery, and is favorable for later recovery. The second insertion body is clamped through the fitting portion. During adjustment, when the second insertion body is rotated, due to a large area of the fitting portion, the fitting portion can prevent the clamping end of the second insertion body from damaging other tissues in rotation. Meanwhile, the fitting portion is also fixed by coupling of the first insertion body and the second insertion body. This omits an operation in which a hole is drilled in the humerus to fix the fitting portion, and further reduces the trauma to the patient in the surgery.

Preferably, the fitting portion is the sheet structure, with a length of 3-6 cm, and a width of 2-4 cm. The fitting portion is totally different from a long fixation plate at an outer side surface of the humerus in the prior art. The long fixation plate in the prior art is mainly intended to fix the humeral head. For the sake of a better fixing effect, the long fixation plate is required to have a length of about 10 cm or more, and a plurality of through holes are formed in a plate body with a length of about 10 cm or more. As shown in FIG. 1, a plurality of through holes are formed in the plate body, and a plurality of bolts pass through the through holes to fix the long fixation plate to the humeral head stably. A plurality of through holes through which the bolts pass to connect the humeral shaft are formed under the plate body, thereby realizing effective fixation. If the long fixation plate is too short (for example, with the length of less than 10 cm), the stable connection cannot be achieved to fix the humeral head. In the present disclosure, the fitting portion of the sheet structure is not intended to fix the humeral head. Since the humeral medullary cavity supporting portion in the repair device takes supporting and fixing effects, the sheet structure is mainly intended to provide the second through hole, so as to insert the second insertion body, and realize the effect of the fitting portion. The length and the width of the sheet structure are reduced greatly. This can alleviate the trauma to the patient when the sheet structure is implanted in the surgery.

Preferably, the position of the sheet structure adjacent to the top side is provided with the rotator cuff suture line through hole. The third through hole for passing through the rotator cuff counteracting bolt is formed at the position of the sheet structure adjacent to the bottom side opposite to the top side. The rotator cuff counteracting bolt can counteract a force of the sutured rotator cuff on the sheet structure, and prevent the sheet structure from upwarping for the force of the rotator cuff to damage other tissues.

Preferably, the axial direction of the third through hole is toward the humeral head within the range of 1-3.5 cm to the lower edge. Since the humeral shaft is relatively firm, and is less likely to be splintered in the proximal humeral fracture, the rotator cuff counteracting bolt can be stably fixed on the humerus.

Preferably, the third through hole is a through hole with leftward incline and downward arrangement. The leftward incline is formed by deviating an axial direction of the through hole to the left side by an angle of 10-30° from a vertical axial direction perpendicular to the fitting surface of the sheet structure. The downward arrangement is formed by deviating the axial direction of the through hole to the bottom side by an angle of 5-40° from the vertical axial direction perpendicular to the fitting surface of the sheet structure. With the third through hole in this direction, after the rotator cuff counteracting bolt is accommodated in the third through hole, the rotator cuff counteracting bolt applies a force to the sheet structure in this direction. Consequently, the fitness that the sheet structure is fitted to the outer sidewall of the humerus is greatly improved, which is favorable for recovery of the fractured site of the patient fitted by the sheet structure.

Preferably, the greater tubercle through hole and the lesser tubercle through hole are formed in the sheet structure. By defining the direction of the greater tubercle through hole and the direction of the lesser tubercle through hole, the in-situ recovery effect of the greater tubercle and the in-situ recovery effect of the lesser tubercle are desirable.

Preferably, the humeral head supporting surface is a supporting plane, and is formed at an angle of 45-50° with a medullary cavity. The humeral head is supported desirably.

Preferably, the greater tubercle supporting member and the humeral head supporting member are split. On one hand, due to the adjustable size of the protrusion of the greater tubercle supporting member, protrusions of various sizes can be produced for greater tubercles of different sizes. For different patients, the greater tubercle supporting members of various sizes can be provided, thereby providing suitable supports for the corresponding patients to improve the postoperative recovery effect. On the other hand, it is found by the applicator in the surgery that the integrated supporting member is implanted into the medullary cavity hardly. Due to the split greater tubercle supporting member and humeral head supporting member, the greater tubercle supporting member and the humeral head supporting member can be separated first. By this time, the humeral medullary cavity supporting portion only having the humeral head supporting member is implanted into the medullary cavity easily.

Preferably, the repair device further includes a locating portion. When the first coupling portion is not coupled to the second coupling portion, the locating portion can be coupled to the third coupling portion. The second locating end of the locating portion can be connected to the guiding portion for a nailing operation. By this time, the third coupling portion provides a desirable support for the guiding portion through the locating portion, which prevents the secondary trauma in the nailing operation to fix the guiding portion or overcomes the defect that the guiding portion is held by another operator, and greatly reduces the time and the cost.

Preferably, each of two sides of the position of the humeral head supporting member toward the greater tubercle supporting member is provided with a convex step to form the first coupling portion. A recess is formed between two convex steps of forming the first coupling portion. Two coupling insertion blind holes arranged side by side are formed in the recess. A threaded blind hole is formed between the two coupling insertion blind holes. The coupling insertion blind holes form the third coupling portion nearly at the same position of the proximal end. That is, the first coupling portion and the third coupling portion are formed outside and inside the position. Two different coupling portions at the same position are coupled to the greater tubercle supporting member or the locating portion. This makes use of the staggered arrangement of the greater tubercle supporting member and the locating portion. That is, the required arrangement is realized at the limited position, and an additional component turns out to be unnecessary to realize the connection, thereby achieving the lower cost obviously. Specifically, with the recess, the weight of the first supporting portion is further reduced, and the material is saved. Meanwhile, by specifically providing the locating portion and the guiding portion, when each component is connected, the stable fixed connection structure for the humeral medullary cavity supporting portion, the locating portion and the guiding portion can be formed.

REFERENCE NUMERALS IN FIGS. 1-11

1: humeral medullary cavity supporting portion, 2: proximal end, 3: humeral head, 4: humeral head supporting surface, 5: first through hole, 6: first insertion body, 7: threaded end, 8: male coupling end, 9: fitting surface, 10: outer side surface, 11: greater tubercle, 12: lesser tubercle, 13: second through hole, 14: second insertion body, 15: female coupling end, 16: clamping end, 17: sheet structure, 18: top side, 19: bottom side, 20: left side, 21: right side, 22: rotator cuff suture line through hole, 23: third through hole, 24: rotator cuff counteracting bolt, 25: threaded tail, 26: end of rotator cuff counteracting bolt, 27: lower edge, 28: humeral shaft within a range of 1-3.5 cm, 29: greater tubercle through hole, 30: lesser tubercle through hole, 31: greater tubercle fixing bolt, 32: lesser tubercle fixing bolt, 33: vertical portion, 34: horizontal through hole, 35: insertion bolt, 36: humeral head supporting member, 37: greater tubercle supporting member, 38: protrusion, 39: locating portion, 40: first locating end, 41: second locating end, 42: guiding portion, 43: upper end, 44: lower end, 45: first guiding through hole, 46: second guiding through hole, 47: convex step, 48: concave step, 49: recess, 50: coupling insertion blind hole, 51: threaded blind hole, 52: guiding insertion blind hole, 53: through hole, 54: hollow rod, 55: insertion protrusion, 56: locating rod, 57: long fixation plate, 58: through hole, 59: bolt, 60: humeral shaft, 61: hollow guiding rod, and 62: guiding needle.

DETAILED DESCRIPTION OF THE EMBODIMENTS

Specific implementations of the present disclosure are described below in detail with reference to the technical solutions and the drawings. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

Figure 1:
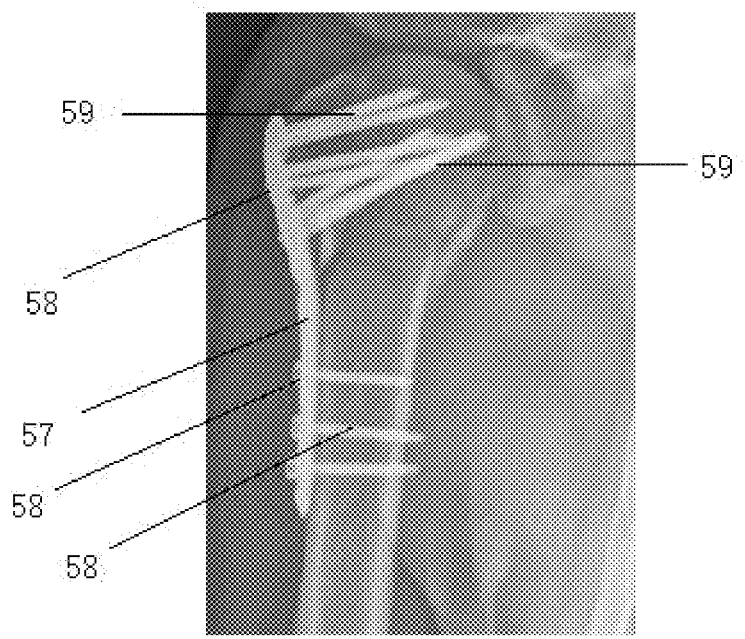
FIG. 1 is a schematic view of an image of a long fixation plate applied to a fracture surgery according to a prior art.
Figure 2:
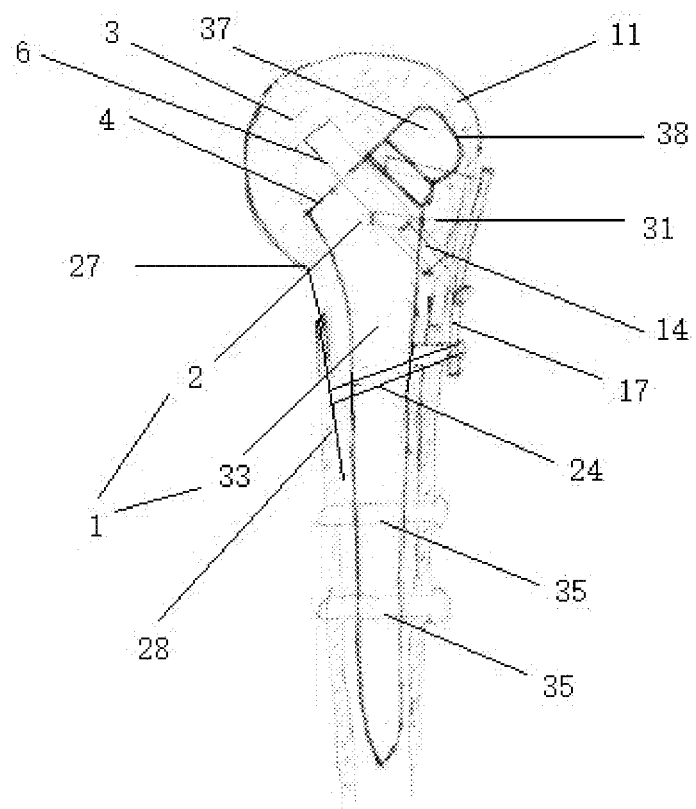
FIG. 2 is a schematic structural view illustrating that a humeral medullary cavity supporting portion and a sheet structure in a repair device are coupled to a humerus according to an implementation of the present disclosure.
Figure 3:
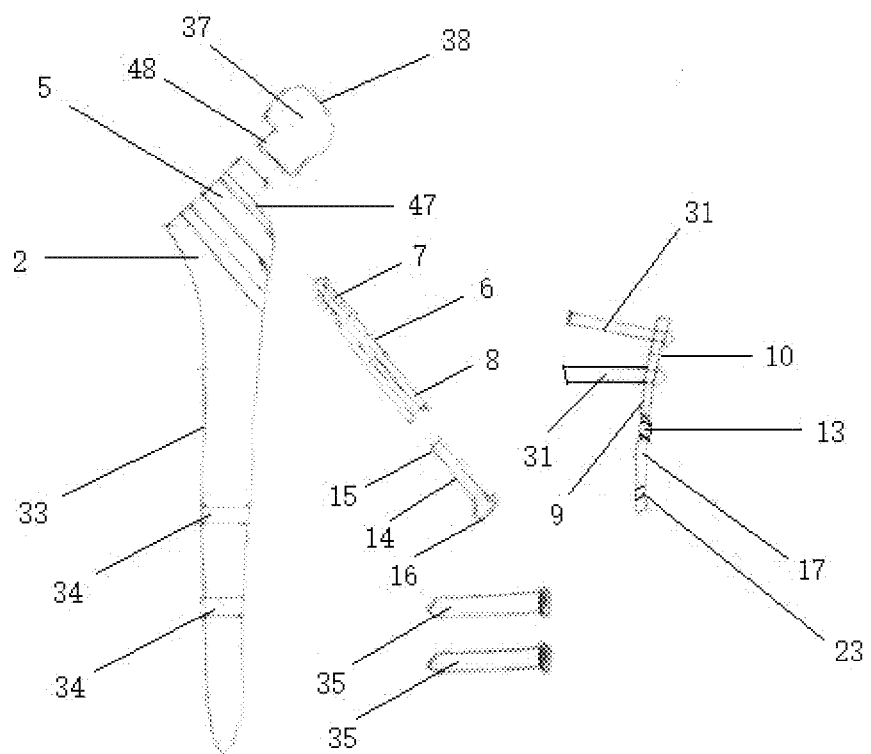
FIG. 3 is an exploded view in FIG. 2.
Figure 4:
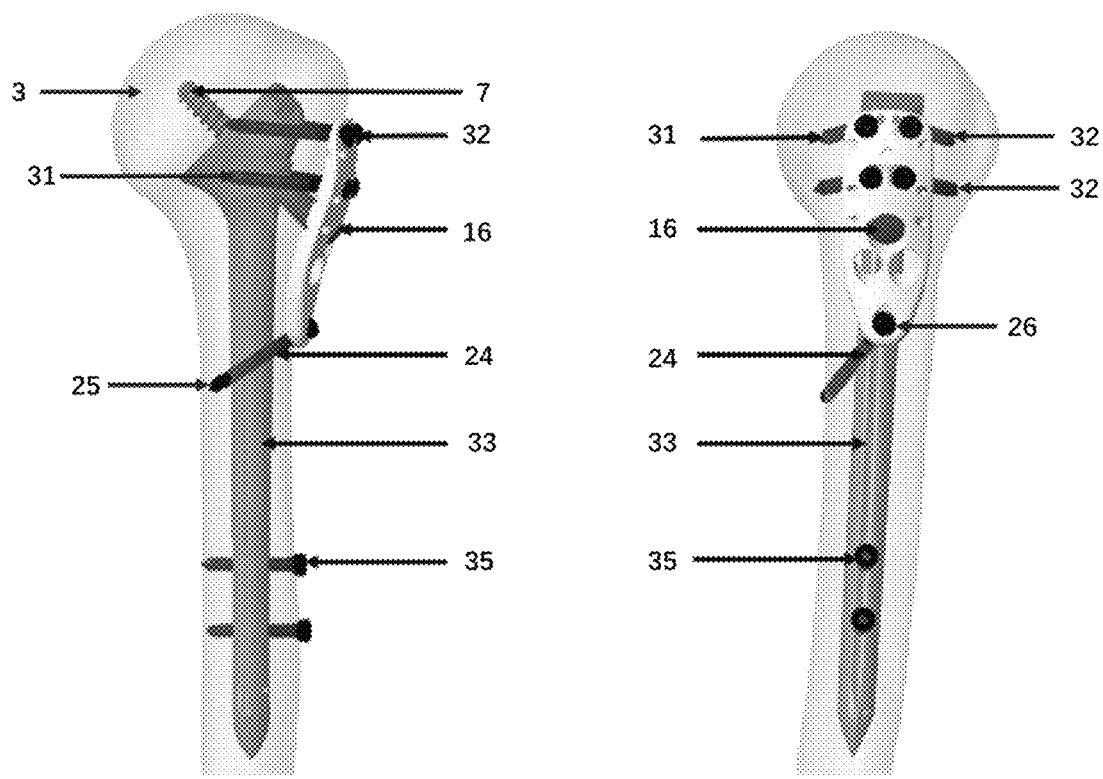
FIG. 4 is a front view and a side view illustrating that a humeral medullary cavity supporting portion and a sheet structure in a repair device are coupled to a humerus according to an implementation of the present disclosure.
Figure 5:
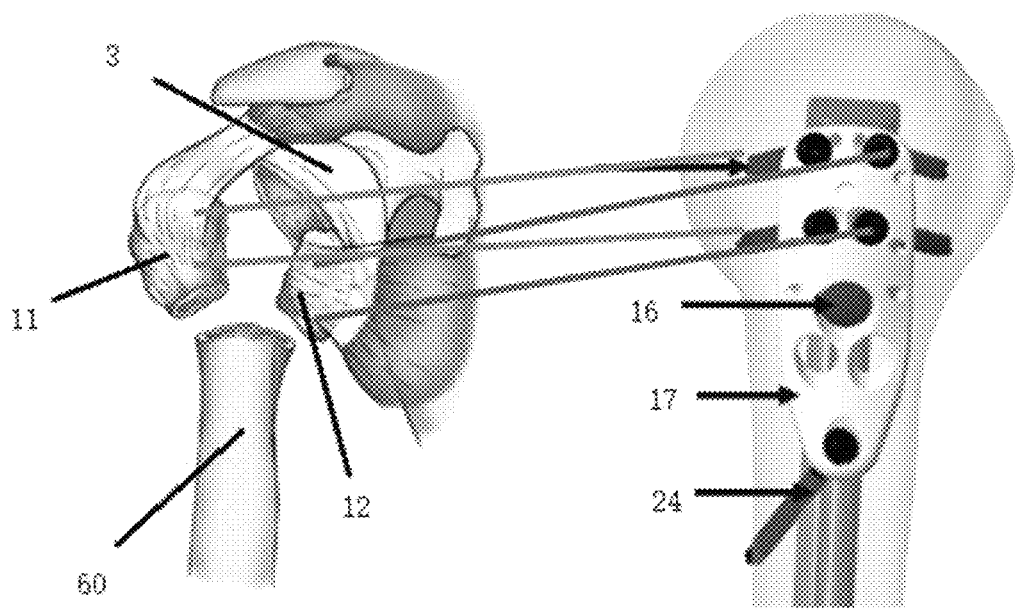
FIG. 5 is a schematic view when a sheet structure is coupled to a humerus.
Figure 6:
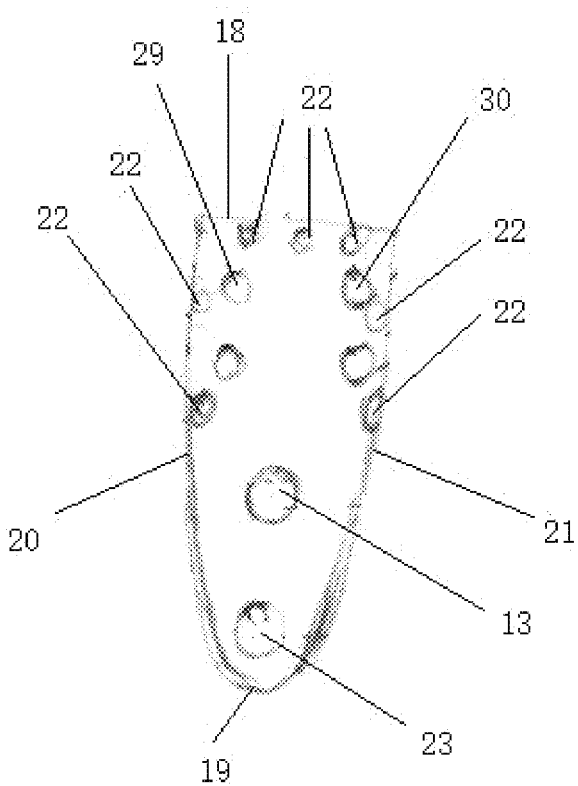
FIG. 6 is a front view of a sheet structure.
Figure 7:
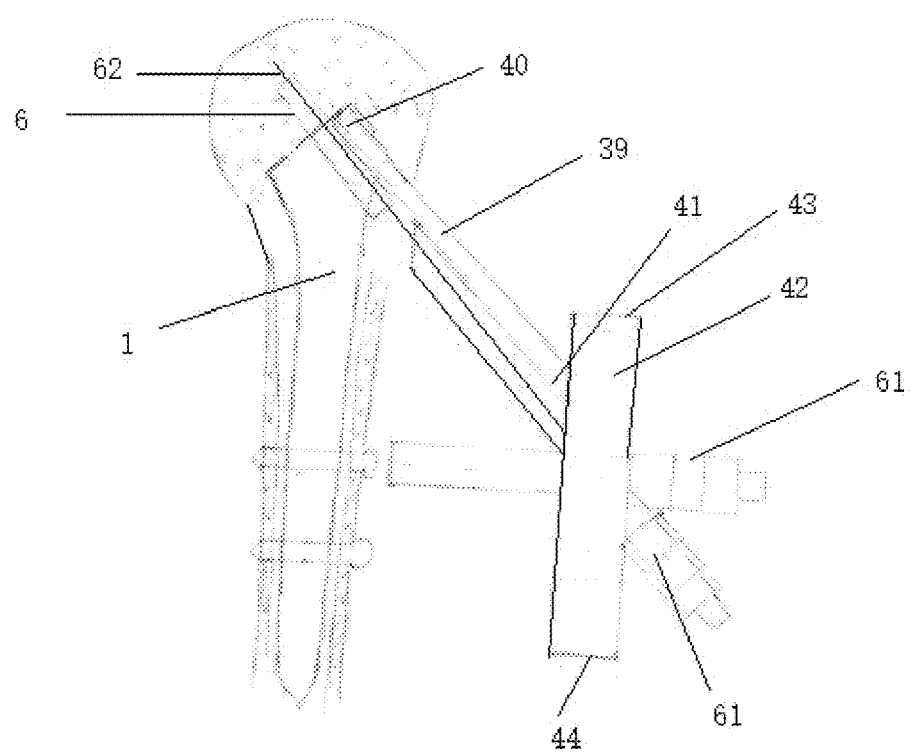
FIG. 7 is a schematic structural view including a humeral medullary cavity supporting portion, a locating portion and a coupling portion in a repair device according to an implementation of the present disclosure.
Figure 8:
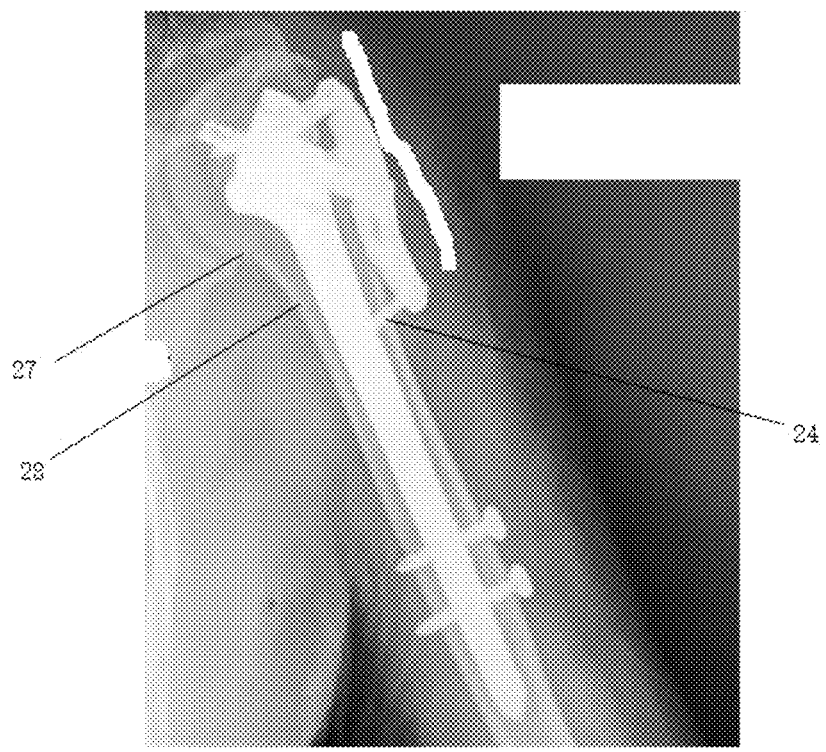
FIG. 8 is a schematic view of an image of a humeral medullary cavity supporting portion and a sheet structure applied to a fracture surgery according to the present disclosure.
Figure 9:
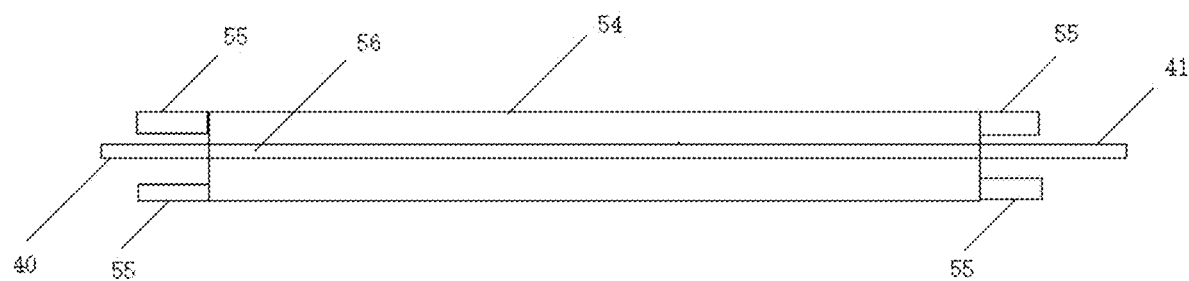
FIG. 9 is a schematic structural view of a hollow rod and a locating rod according to an implementation of the present disclosure.
Figure 10:
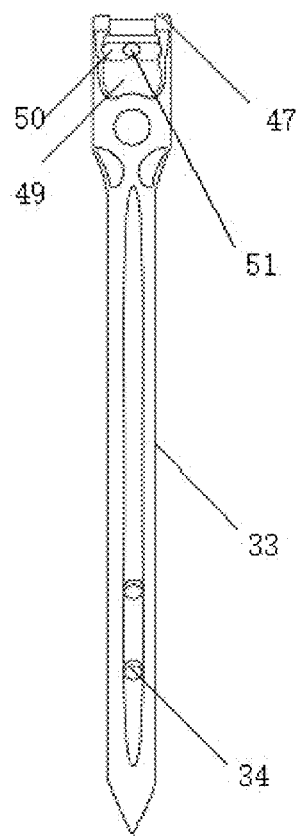
FIG. 10 is a front view of a humeral medullary cavity supporting portion according to an implementation of the present disclosure.
Figure 11:
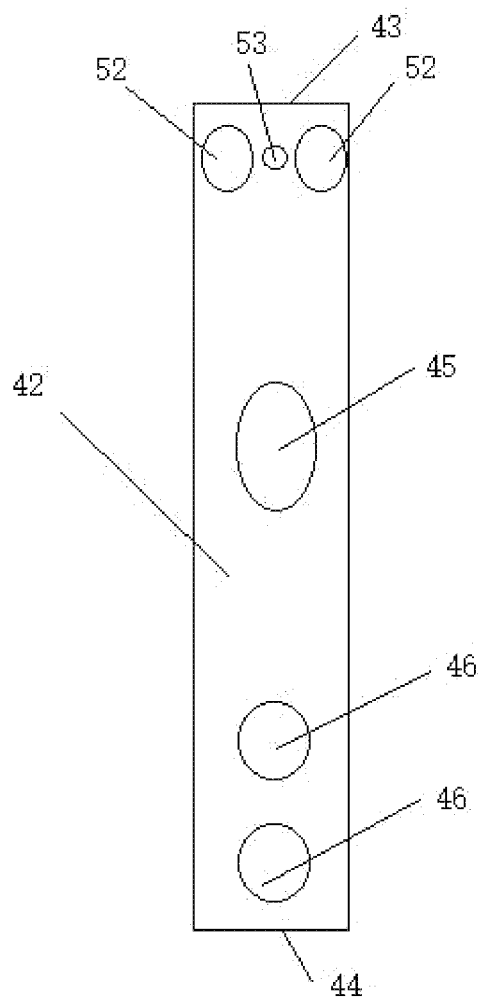
FIG. 11 is a front view of a guiding portion according to the present disclosure.

As shown in FIGS. 1-11, FIG. 1 is a schematic view of an image of a long fixation plate applied to a fracture surgery according to a prior art. FIG. 2 is a schematic structural view illustrating that a humeral medullary cavity supporting portion and a sheet structure in a repair device are coupled to a humerus according to an implementation of the present disclosure. FIG. 3 is an exploded view in FIG. 2. FIG. 4 is a front view and a side view illustrating that a humeral medullary cavity supporting portion and a sheet structure in a repair device are coupled to a humerus according to an implementation of the present disclosure. FIG. 5 is a schematic view when a sheet structure is coupled to a humerus. FIG. 6 is a front view of a sheet structure. FIG. 7 is a schematic structural view including a humeral medullary cavity supporting portion, a locating portion and a coupling portion in a repair device according to an implementation of the present disclosure. FIG. 8 is a schematic view illustrating an image of a humeral medullary cavity supporting portion and a sheet structure applied to a fracture surgery according to the present disclosure. FIG. 9 is a schematic structural view of a hollow rod and a locating rod according to an implementation of the present disclosure. FIG. 10 is a front view of a humeral medullary cavity supporting portion according to an implementation of the present disclosure. FIG. 11 is a front view of a guiding portion according to the present disclosure.

With reference to FIGS. 2-11, in a specific implementation, the repair device includes: humeral medullary cavity supporting portion 1, first insertion body 6, a fitting portion, and second insertion body 14.

The humeral medullary cavity supporting portion 1 is provided with proximal end 2. The proximal end is adjacent to a shoulder. The proximal end 2 includes humeral head supporting surface 4 configured to support humeral head 3 internally. First through hole 5 penetrating through the humeral head supporting surface 4 is formed at the proximal end 2.

Two ends of the first insertion body 6 are respectively provided with threaded end 7 and male coupling end 8. The male coupling end 8 is provided with an internal thread or an external thread. The first insertion body 6 can be inserted into the first through hole 5, with the threaded end 7 allowed to be screwed into the humeral head 3.

The fitting portion includes fitting surface 9 allowed to be fitted to an outer sidewall of a humerus and outer side surface 10 opposite to the fitting surface 9. A position fitted to the outer sidewall of the humerus is a position on the outer sidewall of the humerus away from the humeral head 3 and adjacent to greater tubercle 11 and lesser tubercle 12. Second through hole 13 penetrating through the fitting surface 9 is formed in the fitting portion. When the fitting portion is fitted to the outer sidewall of the humerus, the second through hole 13 is coaxial with the first through hole 5.

Two ends of the second insertion portion 14 are respectively provided with female coupling end 15 and clamping end 16. The female coupling end 15 is provided with an external thread or an internal thread matching with the internal thread or the external thread of the male coupling end 8. When the second insertion body 14 is inserted into the second through hole 13, the clamping end 16 is clamped in the second through hole 13 and located at the outer side surface 10 of the fitting portion, and the female coupling end 15 is coupled to the male coupling end 8, such that a coupled position for the male coupling end 8 and the female coupling end 15 can be adjusted through the clamping end 16, thereby adjusting a position of the humeral head 3.

When the repair device is used by a fractured patient, a structure connected to the humeral head 3, formed by the humeral medullary cavity supporting portion 1, the first insertion body 6, the second insertion body 14 and the fitting portion, and having a high overall stability is formed. While connected to the humeral head 3, the first insertion body 6 is fixedly connected to the second insertion body 14 clamped on the fitting portion, with a high strength. After the repair device is implanted into the body of the patient, the fractured site of the patient almost can take full-range early activities upon a surgery, which is favorable for recovery of the joint at the fracture repaired site. The threaded end 7 of the first insertion body 6 is fixedly connected to the humeral head 3 to realize fixed connection between the repair device and the humeral head 3. The second insertion body 14 is connected to the first insertion body 6 in an adjustable manner. Through the second insertion body 14, the position of the humeral head 3 fixedly connected to the first insertion body 6 can be adjusted. This can realize accurate location on the humeral head 3 at the fracture in the surgery, and is favorable for later recovery. The second insertion body 14 is clamped through the fitting portion. During adjustment, when the second insertion body 14 is rotated, due to a large area of the fitting portion, the fitting portion can prevent the clamping end 16 of the second insertion body 14 from damaging other tissues in rotation. Meanwhile, the fitting portion is also fixed by coupling of the first insertion body 6 and the second insertion body 14. This omits an operation in which a hole is drilled in the humerus to fix the fitting portion, and further reduces the trauma to the patient in the surgery.

In a specific implementation, with reference to FIGS. 2-11, the fitting portion is sheet structure 17. The sheet structure 17 includes top side 18, bottom side 19, as well as left side 20 and right side 21 that are located between the top side 18 and the bottom side 19 and configured to connect the top side 18 and the bottom side 19. When the sheet structure 17 is fitted to the outer sidewall of the humerus, the top side 18 is adjacent to the proximal end, the bottom side 19 is away from the proximal end, the left side 20 is adjacent to the greater tubercle 11, and the right side 21 is adjacent to the lesser tubercle 12. A direction from the top side 18 to the bottom side 19 is a length direction. A length from the top side 18 to the bottom side 19 along the length direction is 3-6 cm. A direction from the left side 20 to the right side 21 is a width direction. A width from the left side 20 to the right side 21 along the width direction is 2-4 cm.

The fitting portion is the sheet structure 17, with a length of 3-6 cm, and a width of 2-4 cm. The fitting portion is totally different from long fixation plate 57 at an outer side surface of the humerus in the prior art. The long fixation plate 57 in the prior art is mainly intended to fix the humeral head 3. For the sake of a better fixing effect, the long fixation plate is required to have a length of about 10 cm or more, and a plurality of through holes 58 are formed in a plate body with a length of about 10 cm or more. As shown in FIG. 1, a plurality of through holes 58 are formed in the plate body, and a plurality of bolts 59 pass through the through holes 58 to connect the long fixation plate 57 to the humeral head 3 stably. A plurality of through holes 58 through which the bolts 59 pass to connect the humeral shaft are formed under the plate body, thereby realizing effective fixation. If the long fixation plate is too short (for example, with the length of less than 10 cm), the stable connection cannot be achieved to fix the humeral head. In the present disclosure, the fitting portion of the sheet structure 17 is not intended to fix the humeral head. Since the humeral medullary cavity supporting portion 1 in the repair device takes supporting and fixing effects, the sheet structure 17 is mainly intended to provide the second through hole 13, so as to insert the second insertion body 14, and realize the effect of the fitting portion. The length and the width of the sheet structure 17 are reduced greatly. This can alleviate the trauma to the patient when the sheet structure 17 is implanted in the surgery.

In the specific implementation, as shown in FIG. 6, a plurality of rotator cuff suture line through holes 22 penetrating through the fitting surface 9 and the outer side surface 10 are formed at a position of the sheet structure 17 adjacent to the top side 18, and configured to allow a rotator cuff suture line to pass through to suture a rotator cuff on the sheet structure 17. Third through hole 23 penetrating through the fitting surface 9 and the outer side surface 10 is formed at a position of the sheet structure 17 adjacent to the bottom side 19. As shown in FIG. 2 and FIG. 4, the repair device further includes rotator cuff counteracting bolt 24. The rotator cuff counteracting bolt 24 can pass through the third through hole 23, with threaded tail 25 allowed to be fixedly connected to the humerus. End 26 of the rotator cuff counteracting bolt is clamped in the third through hole 23 and located at the outer side surface 10 of the sheet structure 17.

The position of the sheet structure 17 adjacent to the top side 18 is provided with the rotator cuff suture line through hole 22. The third through hole 23 for passing through the rotator cuff counteracting bolt 24 is formed at the position of the sheet structure adjacent to the bottom side 19 opposite to the top side 18. The rotator cuff counteracting bolt 24 can counteract a force of the sutured rotator cuff on the sheet structure 17, and prevent the sheet structure 17 from upwarping for the force of the rotator cuff to damage other tissues.

Specifically, as shown in FIG. 2, the humeral head 3 is provided with lower edge 27 away from the proximal end. The lower edge 27 is connected to a humeral shaft located under the lower edge. An axial direction of the third through hole 23 is toward the humeral shaft 28 within a range of 1-3.5 cm to the lower edge, such that the threaded tail 25 of the rotator cuff counteracting bolt 24 can be fixedly connected to the humeral shaft 28 within the range of 1-3.5 cm to the lower edge.

The axial direction of the third through hole 23 is toward the humeral head 28 within the range of 1-3.5 cm to the lower edge. Since the humeral shaft is relatively firm, and is less likely to be splintered in the proximal humeral fracture, the rotator cuff counteracting bolt 24 can be stably fixed on the humerus.

In a specific implementation, the third through hole 23 is a through hole with leftward incline and downward arrangement. The leftward incline is formed by deviating an axial direction of the through hole to the left side 20 by an angle of 10-30° from a vertical axial direction perpendicular to the fitting surface 9 of the sheet structure 17. The downward arrangement is formed by deviating the axial direction of the through hole to the bottom side 19 by an angle of 5-40° from the vertical axial direction perpendicular to the fitting surface 9 of the sheet structure 17.

The third through hole 23 is a through hole with leftward incline and downward arrangement. With the third through hole 23 in the special angle direction, after the rotator cuff counteracting bolt 24 is accommodated in the third through hole, the rotator cuff counteracting bolt 24 applies a force to the sheet structure 17 in this direction. Consequently, the fitness that the sheet structure 17 is fitted to the outer sidewall of the humerus is greatly improved, which is favorable for recovery of the fractured site of the patient fitted by the sheet structure 17.

In a specific implementation, as shown in FIG. 6, the position of the sheet structure 17 adjacent to the top side 18 includes an edge of the sheet structure 17 adjacent to the top side 18 and along the width direction, an edge of the sheet structure 17 adjacent to the top side 18, adjacent to the left side 20 and along the length direction, and an edge of the sheet structure 17 adjacent to the top side 18, adjacent to the right side 21 and along the length direction.

With reference to FIGS. 2-11, in a specific implementation, two greater tubercle through holes 29 penetrating through the fitting surface 9 and the outer side surface 10 are formed at a position of the sheet structure 17 adjacent to the left side 20 along the length direction. Two lesser tubercle through holes 30 penetrating through the fitting surface 9 and the outer side surface 10 are formed at a position of the sheet structure 17 adjacent to the right side 21 along the length direction. The repair device further includes two greater tubercle fixing bolts 31 and two lesser tubercle fixing bolts 32. The greater tubercle fixing bolt 31 can pass through the greater tubercle through hole 29, with a threaded tail allowed to be fixedly connected to the greater tubercle 11. An end of the greater tubercle fixing bolt 31 is clamped in the greater tubercle through hole 29 and located at outer side surface 10 of the sheet structure 17. The lesser tubercle fixing bolt 32 can pass through the lesser tubercle through hole 30, with a threaded tail allowed to be fixedly connected to the lesser tubercle 12. An end of the lesser tubercle fixing bolt 32 is clamped in the lesser tubercle through hole 30 and located at the outer side surface 10 of the sheet structure 17.

In the specific implementation, the greater tubercle through hole 29 is a through hole with leftward incline. The leftward incline is formed by deviating an axial direction of the through hole to the left side 20 by an angle of 10-30° from a vertical axial direction perpendicular to the fitting surface 9 of the sheet structure 17. The lesser tubercle through hole 30 is a through hole with rightward incline. The rightward incline is formed by deviating an axial direction of the through hole to the right side 21 by an angle of 10-30° from the vertical axial direction perpendicular to the fitting surface 9 of the sheet structure 17.

The greater tubercle through hole 29 and the lesser tubercle through hole 30 are formed in the sheet structure 17. By defining the direction of the greater tubercle through hole 29 and the direction of the lesser tubercle through hole 30, the in-situ recovery effect of the greater tubercle 11 and the in-situ recovery effect of the lesser tubercle 12 are desirable.

A shown in FIG. 6, the second through hole 13 is formed at a position of the sheet structure 17 adjacent to a middle along the length direction, and located among the third through hole 23, the greater tubercle through hole 29 and the lesser tubercle through hole 30.

In a specific implementation, with reference to FIGS. 2-11, the humeral medullary cavity supporting portion 1 further includes vertical portion 33 connected to the proximal end 2 and extending away from the proximal end 2. When the sheet structure 17 is coupled and each bolt is provided on the humeral medullary cavity supporting portion 1, the proximal end 2 is provided in the width direction with a width allowed to avoid the greater tubercle fixing bolt 31 and the lesser tubercle fixing bolt 32, and the vertical portion 33 is provided in the width direction with a width allowed to avoid the rotator cuff counteracting bolt 24. At least one horizontal through hole 34 extending along a horizontal direction is formed in the vertical portion 33. The repair device further includes at least one insertion bolt 35 matching with the horizontal through hole 34 in number. The insertion bolt 35 can be in one-to-one correspondence with the horizontal through hole 34, with a threaded end allowed to be screwed into the humeral shaft.

In a specific implementation, to couple the first insertion body 6 and the second insertion body 14, the first insertion body 6 is hollow, such that guiding needle 62 can pass through the first insertion body and the first insertion body 6 is inserted into the first through hole 5 through the guiding needle 62. The internal thread is provided in a hollow rod of the male coupling end 8 of the first insertion body 6. The female coupling end 15 of the second insertion body 14 is a rod provided with the external thread. The external thread can be threadedly connected to the internal thread.

As shown in FIG. 2 and FIG. 3, an axial direction of the first through hole 5 is perpendicular to the humeral head supporting surface 4.

Further, the humeral head supporting surface 4 is a supporting plane, and is formed at an angle of 45-50° with a medullary cavity. The humeral head 3 is supported desirably.

In a specific implementation, the proximal end 2 includes humeral head supporting member 36 and greater tubercle supporting member 37. The humeral head supporting surface 4 is provided on the humeral head supporting member 36. The greater tubercle supporting member 37 and the humeral head supporting member 36 are split. The greater tubercle supporting member 37 is provided with protrusion 38 toward the greater tubercle and allowed to support the greater tubercle 11. A position of the humeral head supporting member 36 toward the greater tubercle supporting member 37 is provided with a first coupling portion. A position of the greater tubercle supporting member 37 toward the humeral head supporting member 36 is provided with a second coupling portion. The first coupling portion is coupled to the second coupling portion, such that the greater tubercle supporting member 37 can be connected to the humeral head supporting member 36.

The greater tubercle supporting member 37 and the humeral head supporting member 36 are split. On one hand, due to the adjustable size of the protrusion 38 of the greater tubercle supporting member 37, protrusions 38 of various sizes can be produced for greater tubercles 11 of different sizes. For different patients, the greater tubercle supporting members 37 of various sizes can be provided, thereby providing suitable supports for the corresponding patients to improve the postoperative recovery effect. On the other hand, it is found by the applicator in the surgery that the integrated supporting member is implanted into the medullary cavity hardly. Due to the split greater tubercle supporting member and humeral head supporting member, the greater tubercle supporting member 36 and the humeral head supporting member 37 can be separated first. By this time, the humeral medullary cavity supporting portion 1 only having the humeral head supporting member 36 is implanted into the medullary cavity easily.

Further, with reference to FIGS. 2-11, the repair device further includes: locating portion 39 and guiding portion 42.

Two ends of the locating portion are respectively provided with first locating end 40 and second locating end 41. A position of the proximal end 2 away from the humeral head supporting surface 4 is provided with a third coupling portion. When the first coupling portion is not coupled to the second coupling portion, the first locating end 40 of the locating portion 39 can be detachably connected to the third coupling portion.

The guiding portion 42 includes upper end 43 and lower end 44. A position of the guiding portion 42 adjacent to the upper end 43 is provided with an upper coupling portion. The second locating end 41 can be detachably connected to the upper coupling portion. First guiding through hole 45 is formed in the guiding portion 42, and configured to guide the first insertion body 6 to be inserted into the first through hole 5. At least one second guiding through hole 46 is further formed in the guiding portion 42. The second guiding through hole 46 is configured to guide the insertion bolt 35 to be inserted into the horizontal through hole 34.

When the first locating end 40 of the locating portion 39 is coupled to the third coupling portion of the proximal end 2 and the second locating end 41 of the locating portion 39 is coupled to the upper coupling portion of the guiding portion 42, a stable structure can be formed by sequentially connecting the humeral medullary cavity supporting portion 1, the locating portion 39 and the guiding portion 42. A direction from the upper end 43 of the guiding portion 42 to the lower end 44 of the guiding portion is a vertical direction parallel to the vertical portion 33. An axial direction of the first guiding through hole 45 coincides with the axial direction of the first through hole 5. An axial of the second guiding through hole 46 coincides with an axial direction of the corresponding horizontal through hole 34.

The repair device further includes the locating portion 39. When the first coupling portion is not coupled to the second coupling portion, the locating portion 39 can be coupled to the third coupling portion. The second locating end 41 of the locating portion 39 can be connected to the guiding portion 42 for a nailing (insertion of the first insertion body and the insertion bolt) operation. By this time, the third coupling portion provides a desirable support for the guiding portion 42 through the locating portion 39, which prevents the secondary trauma in the nailing operation to fix the guiding portion or overcomes the defect that the guiding portion is held by another operator, and greatly reduces the time and the cost.

In a specific implementation, with reference to FIGS. 2-11, each of two sides of the position of the humeral head supporting member 36 toward the greater tubercle supporting member 37 is provided with convex step 47 to form the first coupling portion. A corresponding position of the greater tubercle supporting member 37 toward the convex step 47 is provided with matching concave step 48 to form the second coupling portion. The second coupling portion is lapped on the first coupling portion, such that the humeral head supporting member 36 can fixedly support the greater tubercle supporting member 37. Recess 49 is formed between two convex steps 47 of forming the first coupling portion. Two coupling insertion blind holes 50 arranged side by side are formed in the recess 49. Threaded blind hole 51 is formed between the two coupling insertion blind holes 50. The coupling insertion blind holes 50 form the third coupling portion.

Two guiding insertion blind holes 52 are formed at a position of the guiding portion 42 adjacent to the upper end 43. The guiding insertion blind holes 52 form the upper coupling portion. Through hole 53 is formed between the two guiding insertion blind holes 52.

The locating portion 39 includes hollow rod 54 and locating rod 56. Each of two ends of the hollow rod 54 is provided with two insertion protrusions 55 to form the first locating end 40 and the second locating end 41. The two insertion protrusions 55 of the first locating end 40 are inserted into the two coupling insertion blind holes 50 of the third coupling portion. The two insertion protrusions 55 of the second locating end 41 are inserted into the two guiding insertion blind holes 52 of the guiding portion 42. One end of the locating rod 56 is a threaded end. The threaded end passes through the hollow rod 54 and is threadedly connected to the threaded blind hole 51. The other end of the locating rod 56 is a clamping end, and is clamped at an outer side of an end of the locating rod 56 adjacent to the guiding portion 42.

Each of two sides of the position of the humeral head supporting member 36 toward the greater tubercle supporting member 37 is provided with the convex step 47 to form the first coupling portion. Recess 49 is formed between two convex steps 47 of forming the first coupling portion. Two coupling insertion blind holes 50 arranged side by side are formed in the recess 49. Threaded blind hole 51 is formed between the two coupling insertion blind holes 50. The coupling insertion blind holes 50 form the third coupling portion nearly at the same position of the proximal end 2. That is, the first coupling portion and the third coupling portion are formed outside and inside the position. Two different coupling portions at the same position are coupled to the greater tubercle supporting member 37 or the locating portion 39. This makes use of the staggered arrangement of the greater tubercle supporting member 37 and the locating portion 39. That is, the required arrangement is realized at the limited position, and an additional component turns out to be unnecessary to realize the connection, thereby achieving the lower cost obviously. Specifically, with the recess 49, the weight of the proximal end 2 is further reduced, and the material is saved. Meanwhile, by specifically providing the locating portion 39 and the guiding portion 42, when each component is connected, the stable fixed connection structure for the humeral medullary cavity supporting portion 1, the locating portion 39 and the guiding portion 42 can be formed.

The repair device has the following process approximately in use:

A gap is formed in the fractured site. Through the gap, the humeral medullary cavity supporting portion 1 (the greater tubercle supporting member 37 is not coupled to the proximal end 2. In this way, the gap can be as small as possible) can be implanted into the medullary cavity of the humerus. The humeral head supporting surface 4 is toward an inner side of the humeral head 3. The insertion protrusion 55 at one end of the hollow rod 54 is inserted into the corresponding coupling insertion blind hole 50 of the humeral medullary cavity supporting portion 1. The insertion protrusion 55 at the other end of the hollow rod 54 is inserted into the corresponding guiding insertion blind hole 52 of the guiding portion 42. The locating rod 56 is inserted into the hollow rod 54. One end of the locating rod 56 is a threaded end. The threaded end passes through the hollow rod 54 and is threadedly connected to the threaded blind hole 51. The other end of the locating rod 56 is the clamping end, and is clamped at the outer side of the end of the locating rod 56 adjacent to the guiding portion 42. Therefore, the stable structure is formed by sequentially connecting the humeral medullary cavity supporting portion 1, the locating portion 39 and the guiding portion 42.

Through the stable structure, the first insertion body 6 and the insertion bolt 35 are inserted. Specifically, the hollow guiding rod 61 passes through the first guiding through hole 45 of the guiding portion 42. As shown in FIG. 7, the hollow guiding rod points to the first through hole 5 of the humeral medullary cavity supporting portion 1. A perforation component with one end being shaped as a scissor head is inserted into the hollow guiding rod 61. The perforation component is used to cut apart or drill the humerus and the tissue outside the humerus, such that the hollow guiding rod 61 is docked and connected to the first through hole 5. The guiding needle 62 sequentially passes through the hollow rod 54 and the first through hole 5. The first insertion body 6 that is hollow is guided to the first through hole 5 through the guiding needle 62. The first insertion body 6 is screwed to the humeral head 3 through a hollow cone. This realizes the insertion of the first insertion body 6. As shown in FIG. 7, the hollow guiding rod 61 is implanted into the second guiding through hole 46 of the guiding portion 42. The insertion bolt 35 is inserted into the horizontal through hole 34 in a same operation.

Through the above operations, the first insertion body 6 and the insertion bolt 35 are inserted, and the humeral medullary cavity supporting portion 1 (the greater tubercle supporting member 37 is not coupled to the proximal end 2) is fixedly connected to the humerus. The guiding portion 42, the locating rod 56 and the hollow rod 54 are removed. The greater tubercle supporting member 37 is lapped on the proximal end 2 through cooperation between the concave step 48 of the greater tubercle supporting member and the convex step 47 of the proximal end 2. By this time, the sheet structure 17 is fitted. The second insertion body 14 is inserted into the second through hole 13, such that the second insertion body 14 is coupled to the first insertion body 6. The greater tubercle fixing bolt 31 is coupled to the lesser tubercle fixing bolt 32. The sutured rotator cuff is coupled to the rotator cuff counteracting bolt 24. Therefore, a fixed structure in which the humeral medullary cavity supporting portion 1, the first insertion body 6, the second insertion body 14, the sheet structure 17 and the humerus are extremely stable is formed.

The above implementations are only exemplary in the present disclosure, and not intended to limit the present disclosure. The protection scope of the present disclosure is defined by the claims. Various modifications or equivalent replacements make by those skilled in the art to the present disclosure within the essence and protection scope of the present disclosure also fall within the protection scope of the present disclosure.

What is claimed is:

1. A repair device for a proximal humeral fracture, comprising:
   a humeral medullary cavity supporting portion, wherein the humeral medullary cavity supporting portion is provided with a proximal end, the proximal end is adjacent to a shoulder, the proximal end comprises a humeral head supporting surface configured to support a humeral head internally, and a first through hole penetrating through the humeral head supporting surface is formed at the proximal end;
   a first insertion body, wherein two ends of the first insertion body are respectively provided with a threaded end and a male coupling end, the male coupling end is provided with an internal thread or an external thread, and the first insertion body is allowed to be inserted into the first through hole, with the threaded end allowed to be screwed into the humeral head;
   a fitting portion, wherein the fitting portion comprises a fitting surface allowed to be fitted to an outer sidewall of a humerus and an outer side surface opposite to the fitting surface, a position fitted to the outer sidewall of the humerus is a position on the outer sidewall of the humerus away from the humeral head and adjacent to a greater tubercle and a lesser tubercle, a second through hole penetrating through the fitting surface and the outer side surface is formed in the fitting portion, and when the fitting portion is fitted to the outer sidewall of the humerus, the second through hole is coaxial with the first through hole; and a second insertion body, wherein two ends of the second insertion portion are respectively provided with a female coupling end and a clamping end, the female coupling end is provided with an external thread or an internal thread matching with the internal thread or the external thread of the male coupling end, and when the second insertion body is inserted into the second through hole, the clamping end is clamped in the second through hole and located at the outer side surface of the fitting portion, and the female coupling end is coupled to the male coupling end, such that a coupled position for the male coupling end and the female coupling end is adjusted through the clamping end, thereby adjusting a position of the humeral head.

2. The repair device for the proximal humeral fracture according to claim 1, wherein the fitting portion is a sheet structure; the sheet structure comprises a top side, a bottom side, as well as a left side and a right side that are located between the top side and the bottom side and configured to connect the top side and the bottom side; when the sheet structure is fitted to the outer sidewall of the humerus, the top side is adjacent to the proximal end, the bottom side is away from the proximal end, the left side is adjacent to the greater tubercle, and the right side is adjacent to the lesser tubercle; a direction from the top side to the bottom side is a length direction; a length from the top side to the bottom side along the length direction is 3 cm-6 cm; a direction from the left side to the right side is a width direction; and a width from the left side to the right side along the width direction is 2 cm-4 cm.

3. The repair device for the proximal humeral fracture according to claim 2, wherein a plurality of rotator cuff suture line through holes penetrating through the fitting surface and the outer side surface are formed at a position of the sheet structure adjacent to the top side, and configured to allow a rotator cuff suture line to pass through to suture a rotator cuff on the sheet structure; a third through hole penetrating through the fitting surface and the outer side surface is formed at a position of the sheet structure adjacent to the bottom side; the repair device further comprises a rotator cuff counteracting bolt; the rotator cuff counteracting bolt passes through the third through hole, with a threaded tail allowed to be fixedly connected to the humerus; and an end of the rotator cuff counteracting bolt is clamped in the third through hole and located at the outer side surface of the sheet structure.

4. The repair device for the proximal humeral fracture according to claim 3, wherein the humeral head is provided with a lower edge away from the proximal end; the lower edge is connected to a humeral shaft located under the lower edge; and an axial direction of the third through hole is toward the humeral shaft within a range of 1 cm-3.5 cm to the lower edge, such that the threaded tail of the rotator cuff counteracting bolt is fixedly connected to the humeral shaft within the range of 1 cm-3.5 cm to the lower edge.

5. The repair device for the proximal humeral fracture according to claim 4, wherein the third through hole is a through hole with leftward incline and downward arrangement; the leftward incline is formed by deviating an axial direction of the through hole to the left side by an angle of 10°-30° from a vertical axial direction perpendicular to the fitting surface of the sheet structure; and the downward arrangement is formed by deviating the axial direction of the through hole to the bottom side by an angle of 5°-40° from the vertical axial direction perpendicular to the fitting surface of the sheet structure.

6. The repair device for the proximal humeral fracture according to claim 4, wherein the position of the sheet structure adjacent to the top side comprises an edge of the sheet structure adjacent to the top side and along the width direction, an edge of the sheet structure adjacent to the top side, adjacent to the left side and along the length direction, and an edge of the sheet structure adjacent to the top side, adjacent to the right side and along the length direction.

7. The repair device for the proximal humeral fracture according to claim 4, wherein two greater tubercle through holes penetrating through the fitting surface and the outer side surface are formed at a position of the sheet structure adjacent to the left side along the length direction; two lesser tubercle through holes penetrating through the fitting surface and the outer side surface are formed at a position of the sheet structure adjacent to the right side along the length direction; the repair device further comprises two greater tubercle fixing bolts and two lesser tubercle fixing bolts; the greater tubercle fixing bolt is configured to pass through the greater tubercle through hole, with a threaded tail allowed to be fixedly connected to the greater tubercle; an end of the greater tubercle fixing bolt is clamped in the greater tubercle through hole and located at an outer side surface of the sheet structure; the lesser tubercle fixing bolt is configured to pass through the lesser tubercle through hole, with a threaded tail allowed to be fixedly connected to the lesser tubercle; an end of the lesser tubercle fixing bolt is clamped in the lesser tubercle through hole and located at the outer side surface of the sheet structure.

8. The repair device for the proximal humeral fracture according to claim 7, wherein the greater tubercle through hole is a through hole with leftward incline; the leftward incline is formed by deviating an axial direction of the through hole to the left side by an angle of 10°-30° from a vertical axial direction perpendicular to the fitting surface of the sheet structure; the lesser tubercle through hole is a through hole with rightward incline; and the rightward incline is formed by deviating an axial direction of the through hole to the right side by an angle of 10°-30° from the vertical axial direction perpendicular to the fitting surface of the sheet structure.

9. The repair device for the proximal humeral fracture according to claim 7, wherein the second through hole is formed at a position of the sheet structure adjacent to a middle along the length direction, and located among the third through hole, the greater tubercle through hole and the lesser tubercle through hole.

10. The repair device for the proximal humeral fracture according to claim 8, wherein the humeral medullary cavity supporting portion further comprises a vertical portion connected to the proximal end and extending away from the proximal end; when the sheet structure is coupled and each bolt is provided on the humeral medullary cavity supporting portion, the proximal end is provided in the width direction with a width allowed to avoid the greater tubercle fixing bolt and the lesser tubercle fixing bolt, and the vertical portion is provided in the width direction with a width allowed to avoid the rotator cuff counteracting bolt; at least one horizontal through hole extending along a horizontal direction is formed in the vertical portion; the repair device further comprises at least one insertion bolt matching with the horizontal through hole in number; and the insertion bolt is in one-to-one correspondence with the horizontal through hole, with a threaded end allowed to be screwed into the humeral shaft.

11. The repair device for the proximal humeral fracture according to claim 1, wherein the first insertion body is hollow, such that a guiding needle passes through the first insertion body and the first insertion body is inserted into the first through hole through the guiding needle; the internal thread is provided in a hollow rod of the male coupling end of the first insertion body; the female coupling end of the second insertion body is a rod provided with the external thread; and the external thread is threadedly connected to the internal thread.

12. The repair device for the proximal humeral fracture according to claim 10, wherein an axial direction of the first through hole is perpendicular to the humeral head supporting surface.

13. The repair device for the proximal humeral fracture according to claim 12, wherein the humeral head supporting surface is a supporting plane, and is formed at an angle of 45°-50° with a medullary cavity.

14. The repair device for the proximal humeral fracture according to claim 13, wherein the proximal end comprises a humeral head supporting member and a greater tubercle supporting member; the humeral head supporting surface is provided on the humeral head supporting member; the greater tubercle supporting member and the humeral head supporting member are split; the greater tubercle supporting member is provided with a protrusion toward the greater tubercle and allowed to support the greater tubercle; a position of the humeral head supporting member toward the greater tubercle supporting member is provided with a first coupling portion; a position of the greater tubercle supporting member toward the humeral head supporting member is provided with a second coupling portion; and the first coupling portion is coupled to the second coupling portion, such that the greater tubercle supporting member is connected to the humeral head supporting member.

15. The repair device for the proximal humeral fracture according to claim 14, further comprising:
 a locating portion, wherein two ends of the locating portion are respectively provided with a first locating end and a second locating end; a position of the proximal end away from the humeral head supporting surface is provided with a third coupling portion; and when the first coupling portion is not coupled to the second coupling portion, the first locating end of the locating portion is detachably connected to the third coupling portion; and
 a guiding portion, wherein the guiding portion comprises an upper end and a lower end; a position of the guiding portion adjacent to the upper end is provided with an upper coupling portion; the second locating end is detachably connected to the upper coupling portion; a first guiding through hole is formed in the guiding portion, and configured to guide the first insertion body to be inserted into the first through hole; at least one second guiding through hole is further formed in the guiding portion; and the second guiding through hole is configured to guide the insertion bolt to be inserted into the horizontal through hole;
 wherein when the first locating end of the locating portion is coupled to the third coupling portion of the proximal end and the second locating end of the locating portion is coupled to the upper coupling portion of the guiding portion, a stable structure is formed by sequentially connecting the humeral medullary cavity supporting portion, the locating portion and the guiding portion; and a direction from the upper end of the guiding portion to the lower end of the guiding portion is a vertical direction parallel to the vertical portion, an axial direction of the first guiding through hole coincides with the axial direction of the first through hole, and an axial direction of the second guiding through hole coincides with an axial direction of the corresponding horizontal through hole.

16. The repair device for the proximal humeral fracture according to claim 15, wherein each of two sides of the position of the humeral head supporting member toward the greater tubercle supporting member is provided with a convex step to form the first coupling portion; a corresponding position of the greater tubercle supporting member toward the convex step is provided with a matching concave step to form the second coupling portion; the second coupling portion is lapped on the first coupling portion, such that the humeral head supporting member fixedly supports the greater tubercle supporting member; a recess is formed between two convex steps of forming the first coupling portion; two coupling insertion blind holes arranged side by side are formed in the recess; a threaded blind hole is formed between the two coupling insertion blind holes; and the coupling insertion blind holes form the third coupling portion;
 two guiding insertion blind holes are formed at a position of the guiding portion adjacent to the upper end; the guiding insertion blind holes form the upper coupling portion; and a through hole is formed between the two guiding insertion blind holes; and
 the locating portion comprises a hollow rod and a locating rod; each of two ends of the hollow rod is provided with two insertion protrusions to form the first locating end and the second locating end; the two insertion protrusions of the first locating end are inserted into the two insertion blind holes of the third coupling portion; the two insertion protrusions of the second locating end are inserted into the two guiding insertion blind holes of the guiding portion; one end of the locating rod is a threaded end; the threaded end passes through the hollow rod and is threadedly connected to the threaded blind hole; and the other end of the locating rod is a clamping end, and is clamped at an outer side of an end of the locating rod adjacent to the guiding portion.

* * * * *